United States Patent [19]

Sridhar

[11] Patent Number: 5,720,865
[45] Date of Patent: Feb. 24, 1998

[54] PROCESS FOR THE PREPARATION OF KETO COMPOUNDS

[75] Inventor: Srinivasan Sridhar, Marl, Germany

[73] Assignee: Huels Aktiengesellschaft, Marl, Germany

[21] Appl. No.: 565,043

[22] Filed: Nov. 30, 1995

[30] Foreign Application Priority Data

Feb. 21, 1995 [DE] Germany .................. 195 05 957.3

[51] Int. Cl.$^6$ .................................................. B01D 61/44
[52] U.S. Cl. .................... 204/530; 204/537; 204/541; 560/178
[58] Field of Search ........................... 560/178; 204/530, 204/537, 541

[56] References Cited

U.S. PATENT DOCUMENTS

| | | | |
|---|---|---|---|
| 4,767,870 | 8/1988 | Fujiwara et al. | 549/315 |
| 5,008,465 | 4/1991 | Ballantine et al. | 568/697 |
| 5,153,355 | 10/1992 | Mildenberger et al. | 562/11 |

FOREIGN PATENT DOCUMENTS

| | | |
|---|---|---|
| 4307388 | 9/1994 | Germany . |
| 07067673 | 3/1995 | Japan . |

OTHER PUBLICATIONS

Kulbe et al., "Enzymic . . . Hydrolysates", Ann. N. Y. Acad. Sci., 506 (Biochem. Eng. 5), pp. 543–551 (abstract only), Jan. 1987.

Miyoshi et al., "Condensation . . . Electrodialysis", Chem. Express, 7(11), pp. 893–896 (abstract only), Nov. 1992.

*Primary Examiner*—Gary Geist
*Assistant Examiner*—Rosalynd Keys
*Attorney, Agent, or Firm*—Oblon, Spivak, McClelland, Maier & Neustadt, P.C.

[57] ABSTRACT

Keto compounds are prepared by a condensation reaction in which an enolate is formed, and then a protonation in which the free keto compound is produced. In accordance with the invention, both condensation and protonation are carried out in one step by electrodialysis. Transesterification can also be carried out in the same step.

7 Claims, 1 Drawing Sheet

PROCESS FOR THE PREPARATION OF KETO COMPOUNDS

BACKGROUND OF THE INVENTION

The present invention relates to a novel process for the preparation of keto compounds by condensation reactions.

DISCUSSION OF THE BACKGROUND

Keto compounds are valuable intermediates in the preparation of, for example, heterocycles, pharmaceuticals, plant protection agents and aroma substances.

It is possible, by ester condensation reactions, to convert carboxylic esters to dicarbonyl compounds. In accordance with this method, for example, acetoacetic esters can be prepared from acetic esters. Similarly, using acetic esters, lactones can also be converted into the corresponding acetyl derivatives. In this case the reaction takes place in two steps. In step 1, a condensation is carried out under alkaline conditions, and then the enolate formed is protonated in step 2. The reaction is illustrated by the following scheme, taking as an example the preparation of methyl acetoacetate from methyl acetate:

1. Condensation

methyl acetate

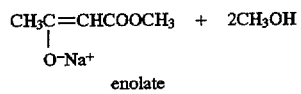

enolate

2. Protonation

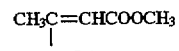

enolate

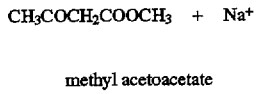

methyl acetoacetate

In accordance with the process in step 2 of the German Patent Application P 44 33 823.6, protonation is carried out by electrodialysis. In this case, for the protonation, use is preferably made of an alcohol which is converted into an alkali metal alcoholate. The alcohol therefore acts as a proton donor which simultaneously traps alkali metal ions.

OBJECTS OF THE INVENTION

One object of the present invention is to simplify the process of German Patent Application (DE) P 44 33 823.6 while retaining its advantages: the recovery of the condensing agent, the avoidance of an acid foreign to the system, and the avoidance of a salt product.

This and other objects will become apparent as the invention becomes better understood by reference to the following detailed description and attached Figure, wherein:

DETAILED DESCRIPTION OF THE INVENTION

Figure 1:
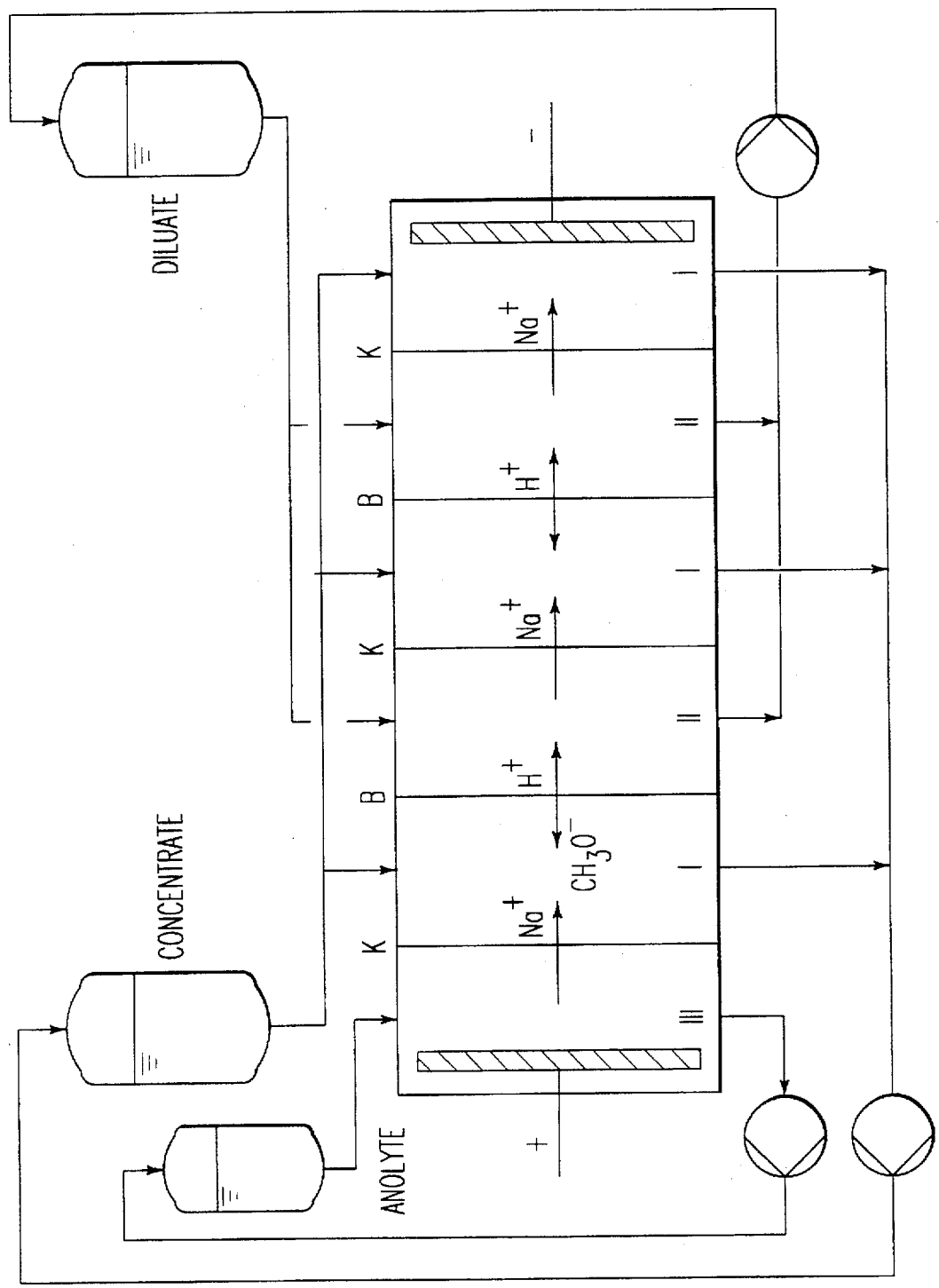
FIG. 1 depicts an electrodialysis cell containing six chambers useful for accomplishing the invention process.

In accordance with the above objects a process is provided wherein both condensation and protonation are carried out in one step by electrodialysis.

Keto compounds which can be prepared in accordance with the present invention are not limited and may be any of simple ketones, diketones, keto esters, keto halides, keto amino acids, keto nitro compounds, etc. They are preferably keto esters, and especially β-keto esters.

Condensation is generally carried out in the presence of alkali metal alcoholates. In this context, suitable alkali metal ions are the sodium and the potassium ion. These alcoholates are generally derived from an alcohol which is also used as a solvent. Suitable examples are alcohols having 1 to 5 carbon atoms, such as methanol, ethanol, isopropanol or tert-butanol, diols such as glycol and butanediol, or triols, such as glycerol. It is also possible to employ alcohol mixtures. The alcohols can contain up to 5% water. They may also contain starting material or product.

Electrodialysis is preferably carried out in the present invention in an electrodialysis cell having 2n+2 chambers, where n is a number from 1 to 60. In particularly preferred cases, n is a number from 1 to 10.

Electrodialysis is preferably carried out at from −20° to +90° C., with particular preference being given to temperatures from 10° to 50° C.

One benefit of the present invention process is that by the combination of condensation and protonation in one process step, the alcoholate consumed in the condensation is recovered during the protonation. Alcoholate can, in this case, be circulated. The process of DE P 44 33 823.6 is simplified further, while retaining the advantages specified therein, in that in the present invention the condensation too is included in the electrodialysis process.

The process of the present invention is illustrated below taking as an example the condensation of methyl acetate to methyl acetoacetate. Of course, the present process is not restricted to this reaction. It is provided only for purposes of illustration.

The present invention process can be elucidated using as an example an electrodialysis cell consisting of 6 chambers, as in FIG. 1: the chambers are each bounded by a cation exchange membrane K and a bipolar membrane B. Instead of the bipolar membrane it is also possible to use a pair of membranes consisting of one anion and one cation exchange membrane.

Into the anode chamber III is fed a methanolic solution of the sodium enolate of methyl acetoacetate. This anolyte forms a separate circuit. Into the chambers I is fed a mixture of methyl acetate and methanol. This mixture is hereafter termed "concentrate". The chambers II are fed with a methanolic solution of the sodium enolate of methyl acetoacetate. This mixture is hereafter termed "diluate".

When an electrical field is applied, the alkali metal ions migrate from the anode chamber and from the chambers II through the cation exchange membranes K, in the direction of the cathode, into the chambers I, where they form the alcoholate. The production of the condensing agent leads to the condensation of the carboxylic ester in these chambers. The chambers I therefore represent reactor chambers in which the methyl acetoacetate is produced in the enolate form. Protons pass through the bipolar membranes B. Therefore, the protonation of the enolate takes place in the chambers II, thereby producing the free methyl acetoacetate.

The condensation is an equilibrium reaction and requires continuous removal of the alcohol produced. For example, the concentrate is subjected to electrodialytic treatment until the condensation has almost reached equilibrium. It is subsequently led into an external tank (not indicated in FIG. 1) which acts as reactor. The reaction can be carried out at any suitable temperature, even higher than 90° C. The reaction is then followed by distillative removal of the alcohol optionally by means of an entraining agent. The unreacted acetic ester which remains is employed as starting material for the next batch.

In a preferred embodiment of the process according to the invention, the concentrate tank is maintained at an elevated temperature in order to accelerate the condensation. The abovementioned distillation can then take place directly from the concentrate tank with a column mounted on it. By means of such an embodiment it is possible for condensation and protonation to be carried out rapidly and be harmonized with one another.

Following a batchwise electrodialysis, the product solution is run off from the diluate tank and the tank is filled with the freshly produced condensation product (still in the from of the Na enolate) from the concentrate tank. The spent anolyte is replaced by the corresponding amount of the diluate which has been run off. In this way, the sodium ions are retained in the system. The net equation of the above process is:

The larger remainder of the diluate is passed to a distillation stage in order to free the acetoacetic ester from methanol, in so far as this has not already been done in the concentration tank. After the concentration tank has been filled with fresh methyl acetate solution, the next batchwise reaction can be commenced.

Since the condensation is an equilibrium reaction, the attempt may be made to continually remove the products formed from the system to increase yield. In a further preferred embodiment of the process according to the invention, after just a slight conversion in the electrodialysis unit, the concentrate stream is introduced into the diluate chambers II. Here, the protonation of the small quantity of enolate which has just been produced takes place. In this way, the enolate is taken out of the chemical equilibrium with the condensation. The diluate stream is then subjected to distillation in order to remove the alcohol produced as well. Subsequently, the solution is passed back into the concentrate tank in order to continue the reaction. In this embodiment, continual condensation and protonation take place in a circuit.

Furthermore, the process according to the invention can also be used to carry out condensation and transesterification simultaneously. This is possible when the alcohol of the concentrate is different from the alcohol of the diluate. Thus, for example, from methyl acetate it is possible to prepare the ethyl acetoacetate.

The example which follows is intended to further illustrate the invention.

EXAMPLE 1

In accordance with the description which has already been given, a stack is used which is equipped with four circuits, namely two electrode circuits, a diluate circuit and a concentrate circuit. The membranes come from TOKUYAMA SODA Corp. Instead of a bipolar membrane, a membrane pair consisting of one anion and one cation exchange membrane is employed. The sequence of membranes, from the anode to the cathode, is as follows: a cation exchange membrane (type C66-10F), a membrane pair (type AM 1 and CM 1) and another cation exchange membrane (type C66-10F), followed by the cathode. The effective membrane area per membrane is 100 $cm^2$. The experiment takes place at room temperature. Only the concentrate circuit, in which condensation takes place, is maintained at 45° C.

The initial anolyte charge comprises 1,388 g of a 6 percent by weight solution of sodium methanolate in methanol. The catholyte consists initially of a 1.23 percent by weight solution of sodium methanolate in methanol. The diluate used (protonation circuit) comprises 1,282 g of a 10 percent by weight solution of the sodium enolate of methyl acetoacetate in methanol. The concentrate employed (reaction circuit) comprises 1,450 g of a 15.78 percent by weight solution of methyl acetate. The solution additionally contains 0.5 percent by weight of sodium methanolate as conductive salt.

The solutions are pumped continuously around appropriate circuits. Between the electrodes, a voltage of 120 V is applied. The experiment is terminated after 26 hours and 40 minutes, at which point the samples from the circuits are analyzed. In the concentrate circuit, 12.4 g of the Na enolate of the acetoacetic ester are produced. in the same period, in the diluate circuit, 11.7 g of free acetoacetic ester are prepared. From the results it is evident that simultaneous condensation and protonation according to the invention has occurred.

This application is based on German Patent Application 195 05 957.3 filed Feb. 21, 1995, incorporated herein by reference.

What is claimed as new and is desired to be secured by Letters Patent of the United States is:

1. A process for the preparation of keto compounds by condensation, wherein condensation and protonation are carried out in one process step by electrodialysis.

2. The process according to claim 1, wherein keto esters are prepared.

3. The process according to claim 1, wherein condensation and protonation are carried out in an electrodialysis cell having 2n+2 chambers, where n is a number from 1 to 60.

4. The process according to claim 3, wherein n is a number from 1 to 10.

5. The process according to claim 1, wherein condensation and protonation are carried out at from −20 ° to +90° C.

6. The process according to claim 1, wherein condensation and protonation are carried out at from 10° to 50° C.

7. The process according to claim 2, wherein transesterification is carried out in the same step with condensation and protonation by electrodialysis.

* * * * *